US010959057B2

(12) United States Patent
Kim et al.

(10) Patent No.: US 10,959,057 B2
(45) Date of Patent: Mar. 23, 2021

(54) SYSTEM FOR DETECTING ROAMING

(71) Applicant: Korea Institute of Science & Technology Information, Daejeon (KR)

(72) Inventors: Jung Joon Kim, Seoul (KR); Hong Woo Chun, Seoul (KR); Seon Ho Kim, Seoul (KR)

(73) Assignee: KOREA INSTITUTE OF SCIENCE & TECHNOLOGY INFORMATION, Daejeon (KR)

( * ) Notice: Subject to any disclaimer, the term of this patent is extended or adjusted under 35 U.S.C. 154(b) by 0 days.

(21) Appl. No.: 16/908,663

(22) Filed: Jun. 22, 2020

(65) Prior Publication Data

US 2020/0322759 A1 Oct. 8, 2020

Related U.S. Application Data

(63) Continuation of application No. PCT/KR2019/013259, filed on Oct. 10, 2019.

(30) Foreign Application Priority Data

Oct. 10, 2018 (KR) .......................... 10-2018-0120616

(51) Int. Cl.
*H04W 4/02* (2018.01)
*H04W 4/029* (2018.01)
(Continued)

(52) U.S. Cl.
CPC ............. *H04W 4/029* (2018.02); *A61B 5/002* (2013.01); *A61B 5/024* (2013.01); *A61B 5/112* (2013.01);
(Continued)

(58) Field of Classification Search
CPC ....... H04W 4/029; H04W 4/33; H04W 4/027; A61B 5/002; A61B 5/024; A61B 5/1112; A61B 5/1113; A61B 5/112; A61B 5/7264
See application file for complete search history.

(56) References Cited

U.S. PATENT DOCUMENTS

2019/0108753 A1* 4/2019 Kaiser .................... H04W 4/02

FOREIGN PATENT DOCUMENTS

JP 10-221426 A 8/1998
JP 2016-526953 A 9/2016
(Continued)

OTHER PUBLICATIONS

International Search Report and Written Opinion in PCT/KR2019/013259, dated Apr. 13, 2020.
(Continued)

*Primary Examiner* — Curtis B Odom
(74) *Attorney, Agent, or Firm* — Sheppard Mullin Richter & Hampton LLP

(57) ABSTRACT

A method for detecting whether a user's roaming has occurred is provided. The method may be performed by a roaming detection server and comprises receiving location data of the user from a terminal of the user, determining whether the user may be located indoors by using the location data of the user, and determining a use of a building in which the user may be located using use information of the building based on the user being located indoors, and detecting whether the user's roaming has occurred based on a predetermined condition, wherein it may be detected that the roaming has occurred based on the building in which the user may be located not being a building of a predetermined use.

20 Claims, 12 Drawing Sheets

(51) Int. Cl.
*H04W 4/33* (2018.01)
*A61B 5/00* (2006.01)
*A61B 5/024* (2006.01)
*A61B 5/11* (2006.01)

(52) U.S. Cl.
CPC .......... *A61B 5/1112* (2013.01); *A61B 5/1113* (2013.01); *A61B 5/7264* (2013.01); *H04W 4/027* (2013.01); *H04W 4/33* (2018.02)

(56) References Cited

FOREIGN PATENT DOCUMENTS

| KR | 10-1088226 B1 | 11/2011 |
| KR | 20110133476 A | 12/2011 |
| KR | 10-20150050224 A | 5/2015 |
| KR | 10-1548729 B1 | 9/2015 |
| KR | 10-20160052999 A | 5/2016 |
| KR | 10-2017-0048920 A | 5/2017 |
| KR | 10-2018-0014919 A | 2/2018 |
| KR | 10-1996212 B1 | 10/2019 |

OTHER PUBLICATIONS

Kim, Jamje, et al., "Mobile Reader Selection for Improving Precision of Location Estimation in RTLS," Journal of KIISE: Computing Practices and Lettersm 16(1), Jan. 2010, pp. 45-49.

\* cited by examiner

SYSTEM FOR DETECTING ROAMING

CROSS-REFERENCE TO RELATED APPLICATION

This application is a Continuation of International Application No. PCT/KR2019/013259 filed Oct. 10, 2019, which claims benefit of priority to Korean Patent Application No. 10-2018-0120616 filed Oct. 10, 2018, the entire content of which is incorporated herein by reference.

BACKGROUND

1. Technical Field

The present disclosure relates to a system for detecting roaming. More specifically, it relates to a system for detecting roaming that detects whether a user has roamed by using walking speed information and heart rate information of the user as well as location information of the user.

2. Description of the Related Art

With the aging of modern society, the disease of senile dementia patients with memory impairment has emerged as a serious medical and social problem. More specifically, the elderly aged 65 and over were 540,000 in 2000, but doubled to 1.02 million in 2012, and are expected to rapidly increase to 1.15 million in 10 years and 2.34 million in 2030. In addition, the prevalence of dementia among the elderly over 65 is also 8.6%, and it is known that 450,000 elderly people suffer from dementia.

In general, the first symptom most patients with dementia suffer from is memory impairment. Based on these memory disorders becoming severe, the number of cases in which names and phone numbers are not well remembered increases or problems in intellectual abilities occur, resulting in a significant decrease in sense of direction or spatial perception. In addition, one may often get lost, or one may frequently get lost, even on a familiar road (i.e., roaming symptoms).

As such, it is often the case that people with dementia get lost because of a sense of disorientation based on leaving their homes. Some of them return home after being confirmed by their guardians. However, some are missing, causing the guardians to suffer a lot of material and time loss to find patients with dementia. There is a problem that may cause severe mental damage to the guardian.

In order to solve this problem, in the related art, it is determined that the dementia patient is roaming through receiving the location information of the dementia patient from a terminal such as a mobile phone of the dementia patient or a wearable device worn by the dementia patient.

However, in the conventional method for detecting roaming using the location information, based on the patient moving indoors, such as a building to which an indoor positioning technology is not applied, the exact location information is not received from the dementia patient's wearable device. There may be a problem of not detecting the roaming symptoms occurring indoors. In addition, based on the patient with dementia not leaving a certain area while exceeding a certain time, it is determined to be roaming. There may be a problem in that based on the patient with dementia being located indoors and a certain period of time has elapsed, it is determined that the roaming has occurred regardless of the actual roaming symptoms.

Additionally, it does not take into account the individual characteristics of the dementia patient, but simply detects roaming using the location information. There may be a problem in that the reliability of a result value is poor in that the roaming may be detected despite the non-roaming situation.

SUMMARY

Aspects of the present disclosure provide a roaming detection server and a method for detecting roaming using the same, in which based on a user being located indoors, it uses location information of the user to detect whether roaming occurs depending on the use or purpose of a building where the user is located, thereby preventing indiscriminate detection of roaming due to the fact that a dementia patient stays in one place for a long time.

Aspects of the present disclosure also provide a roaming detection server and a method for detecting roaming using the same, in which even based on a user being located in a building where an indoor positioning technology is not applied to and is difficult to measure an indoor location, it detects roaming using changes in a walking speed and a heart rate of the user, thereby enabling to accurately detect roaming not only outdoors but also indoors.

Aspects of the present disclosure also provide a roaming detection server and a method for detecting roaming using the same, in which a walking speed and a heart rate of a user are personalized and stored, and it is detected that the user in a roaming state changes the walking speed or the heart rate changes, thereby enabling to detect roaming in consideration of personal characteristics of the user as well as location information of the user.

However, aspects of the present disclosure are not restricted to those set forth herein. The above and other aspects of the present disclosure will become more apparent to one of ordinary skill in the art to which the present disclosure pertains by referencing the detailed description of the present disclosure given below.

According to the present disclosure, a method for detecting whether a user's roaming has occurred is provided. The method may be performed by a roaming detection server and comprises receiving location data of the user from a terminal of the user, determining whether the user is located indoors by using the location data of the user, and determining a use of a building in which the user is located using use information of the building based on the user being located indoors, and detecting whether the user's roaming has occurred based on a predetermined condition, wherein it is detected that the roaming has occurred based on the building in which the user is located not being a building of a predetermined use. The detecting may further comprise calculating a walking index using the user's gait data, generating a gait model for learning the calculated walking index using machine learning, and detecting whether the user's roaming has occurred using the generated gait model, and calculating the walking index using Equation 1 below:

$$\text{walking index} = (\text{amount of change in direction} + \alpha) \times (\text{amount of change in speed} + \beta)$$

where, the $\alpha$ and $\beta$ are arbitrary constant values exceeding 1.

According to the present disclosure, a roaming detection server is provided. The server comprises an interface for receiving location data of a user from a terminal of the user, a location determination unit for determining whether the user is located indoors by using the location data of the user, and determining a use of a building in which the user is located using use information of the building based on the user being located indoors, and a roaming detection unit for detecting whether the user's roaming has occurred based on a predetermined condition, wherein it is detected that the roaming has occurred based on the building in which the user is located not being a building of a predetermined use. The roaming detection unit may calculate a walking index using the user's gait data, generate a gait model for learning the calculated walking index using machine learning, detect whether the user's roaming has occurred using the generated gait model, and calculate the walking index using Equation 1 below:

walking index=(amount of change in direction+α)× (amount of change in speed+β)

where, the α and β are arbitrary constant values exceeding 1.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION OF THE EMBODIMENTS

Figure 1:
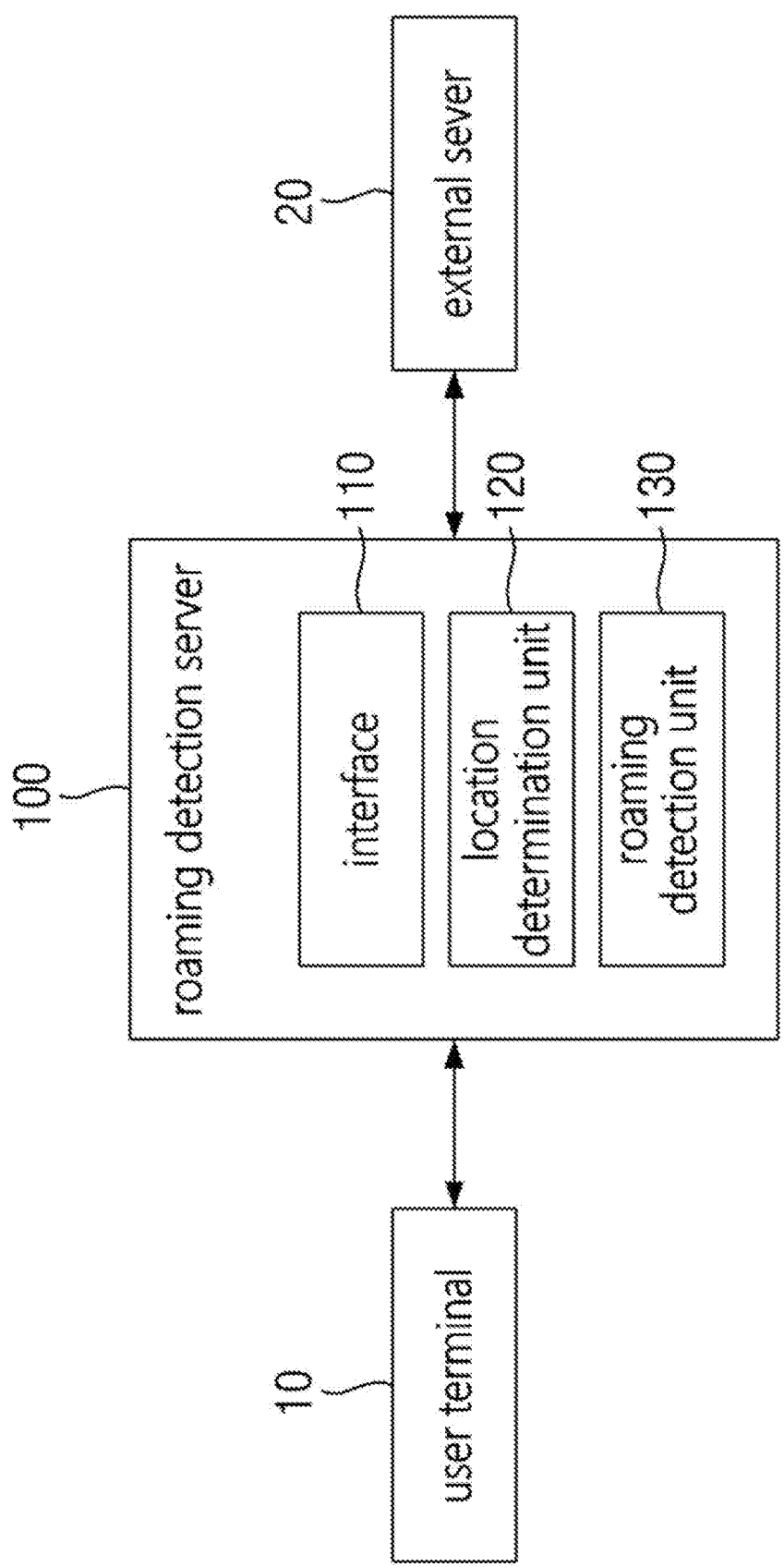
FIG. 1 is a diagram schematically showing the components of a roaming detection server 100 according to an embodiment of the present disclosure.

Hereinafter, embodiments of the present disclosure will be described with reference to the attached drawings. Advantages and features of the present disclosure and methods of accomplishing the same may be understood more readily by reference to the following detailed description of embodiments and the accompanying drawings. The present disclosure may, however, be embodied in many different forms and should not be construed as being limited to the embodiments set forth herein. Rather, these embodiments are provided so that this disclosure will be thorough and complete and will fully convey the disclosure to those skilled in the art, and the present disclosure will be defined by the appended claims.

In adding reference numerals to the components of each drawing, it should be noted that the same reference numerals are assigned to the same components as much as possible even though they are shown in different drawings. In addition, in describing the presently disclosed technology, based on it being determined that the detailed description of the related well-known configuration or function may obscure the gist of the presently disclosed technology, the detailed description thereof will be omitted.

Unless otherwise defined, all terms used in the present specification (including technical and scientific terms) may be used in a sense that can be commonly understood by those skilled in the art. In addition, the terms defined in the commonly used dictionaries are not ideally or excessively interpreted unless they are specifically defined clearly. The terminology used herein is for the purpose of describing embodiments and is not intended to be limiting of the presently disclosed technology. In this specification, the singular also includes the plural unless specifically stated otherwise in the phrase.

In addition, in describing the component of this presently disclosed technology, terms, such as first, second, A, B, (a), (b), can be used. These terms are for distinguishing the components from other components, and the nature or order of the components is not limited by the terms. If a component is described as being "connected," "coupled" or "contacted" to another component, that component may be directly connected to or contacted with that other component, but it should be understood that another component also may be "connected," "coupled" or "contacted" between each component.

Hereinafter, some embodiments of the presently disclosed technology will be described in detail with reference to the accompanying drawings.

FIG. 1 is a diagram schematically showing the components of a roaming detection server 100 according to an embodiment of the present disclosure.

Referring to FIG. 1, the roaming detection server 100 according to the embodiment of the present disclosure may include an interface 110, a location determination unit 120, and a roaming detection unit 130.

Here, the roaming detection server 100 shown in FIG. 1 is according to an embodiment, and its components are not limited to the embodiment shown in FIG. 1. It is noted that it may be added, changed, or deleted. Hereinafter, the configuration and operation of the roaming detection server 100 according to the embodiment of the present disclosure will be described with reference to FIGS. 1 and 2.

Figure 2:
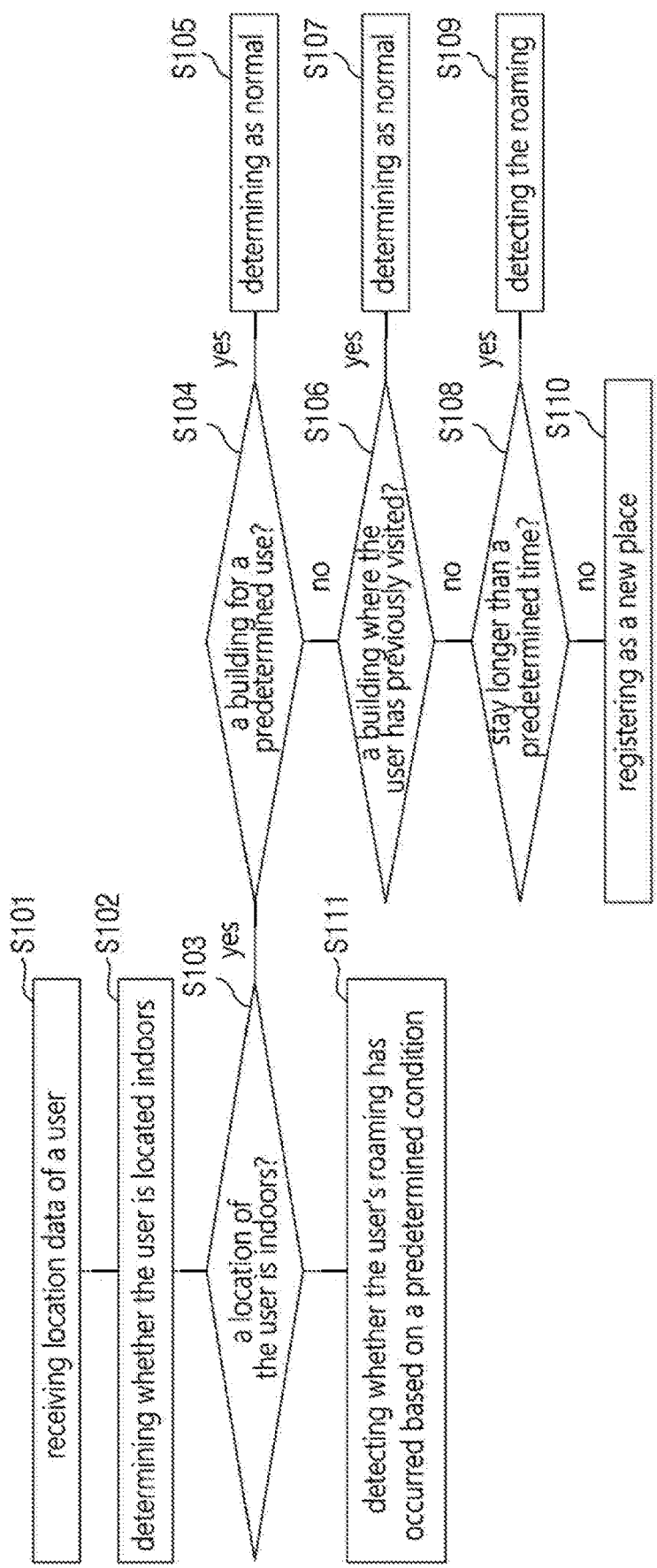
FIG. 2 is a flowchart for explaining a configuration in which the roaming detection server 100 according to the embodiment of the present disclosure detects roaming depending on the use of a building.

FIG. 2 is a flowchart for explaining a configuration in which the roaming detection server 100 according to the embodiment of the present disclosure detects roaming depending on the use or purpose of a building.

Referring to FIGS. 1 and 2, first, receiving location data of a user through the interface 110 may be performed (S101).

The interface 110 may communicate and connect with a user terminal 10 of the user and an external server 20. The interface 110 may receive various data from the user terminal 10 and the external server 20, and may provide various result data generated by the roaming detection server 100 to the user terminal 10 and the external server 20.

The interface 110 may communicate with and connect to the user terminal 10 to receive location data of the user. Here, the user terminal 10 may be a smart phone carried by the user or a wearable device worn by the user, and the location data refers to GPS data including location information of the user measured from a GPS sensor provided in the user terminal 10. However, it is not limited thereto, and the interface 110 may communicate with and connect to a building management system (BMS) of a building in which the user may be located. Further, the interface 110 may receive the location data of the user measured from an indoor positioning system provided in the BMS, such as a location measurement scheme using a Wi-Fi protected setup (WPS) scheme.

In addition, the interface 110 may communicate with and connect to the external server 20 to receive use information of a building including geographic information system (GIS) information. Here, the external server 20 may be a server of the Ministry of Land, Infrastructure, and Transport that stores GIS information.

Next, the location determination unit 120 may perform determining whether the user may be located indoors by using the location data of the user received in step S101 (S102), and as a result of determining whether a location of the user may be indoors, based on the user being indoors, determining the use or purpose of a building where the user may be located (S103).

The location determination unit 120 may determine whether the user may be currently indoors using the location data of the user received from the user terminal 10 through the interface 110.

Based on it being determined that the user may be located indoors, the location determination unit 120 may determine the use of the building where the user may be located based on the use information of the building received from the external server 20.

Here, the use of the building means that the types of buildings are grouped by similar structure, purpose of use, and form, and may include housing, religious facilities, sales facilities, medical facilities, educational facilities, sports facilities, lodging facilities, factories, power generation facilities, tourist resting facilities, or the like. In addition, the use of each classified building may be subdivided into churches, power plants, movie theaters, factories, schools, detached houses, parking lots, department stores (shopping malls), public houses, or the like.

In an embodiment, the location determination unit 120 may generate a map including information on the use of the building by mapping the GIS information provided from the external server 20 with a map. The location determination unit 120 may apply the location data of the user received from the user terminal 10 to the map to which the GIS information may be mapped, and receive the use of the building corresponding to the location of the user in the map to which the GIS information may be mapped, thereby determining the use of the building where the user may be currently located. For example, based on the use of the building corresponding to the location of the user being a shopping mall, the location determination unit 120 may determine that the current location of the user may be inside the shopping mall.

Next, the roaming detection unit 130 may perform determining whether roaming occurs depending on the use or purpose of the building (S104).

The roaming detection unit 130 detects whether the user may be roaming based on a predetermined condition, in which based on the use or purpose of the building not being a predetermined use or purpose, it may be detected that roaming has occurred.

Here, detecting whether roaming of the user occurs based on the predetermined condition refers to conditions for detecting roaming for the user who shows roaming symptoms depending on whether the user may be hovering around, whether the user may be moving without any purpose, whether a walking speed of the user may be rapidly changing, whether the user continues to move on the same path, or whether the user walks in a circle. Hereinafter, a configuration in which the roaming detection unit 130 detects a roaming operation will be described with reference to FIG. 3.

Figure 3:
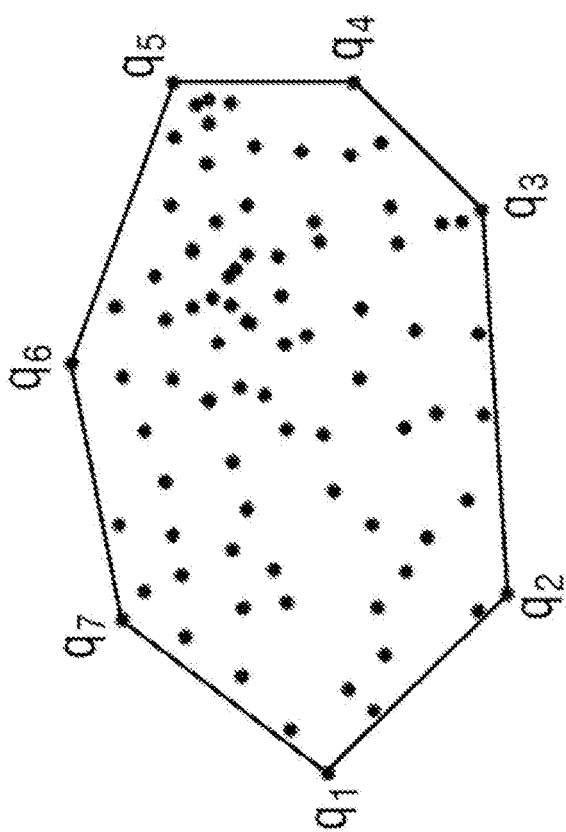
FIG. 3 is a diagram for explaining a convex hull algorithm performed by the roaming detection server 100 according to the embodiment of the present disclosure.
Figure 3:
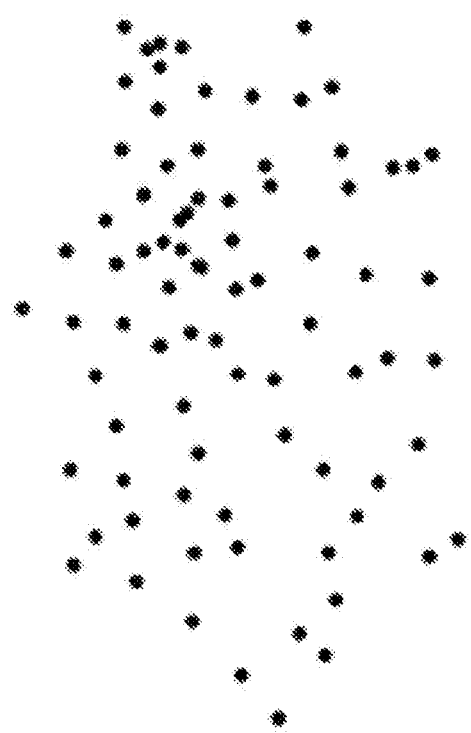

FIG. 3 is a diagram for explaining a convex hull algorithm performed by the roaming detection server 100 according to the embodiment of the present disclosure.

Referring to FIG. 3, the roaming detection unit 130 may detect whether the user may be roaming using the convex hull algorithm. For example, the roaming detection unit 130 may generate a set of places where the user may be located by displaying a location where the user may be located at a certain point in time as shown in FIG. 3A using the location data of the user. Thereafter, the roaming detection unit 130 may form a polygon with a shape shown in FIG. 3B by connecting the outermost points in the set of the location data of the user received for a period of time. Here, the convex hull algorithm performed by the roaming detection server 100 according to the embodiment of the present disclosure is according to an embodiment. However, it is not limited thereto, and any method for determining whether the user shows the roaming symptoms may be applied.

Based on the location data of the user, based on the user not deviating from within the polygon shown in FIG. 3B while the location of the user exceeds a predetermined time, the roaming detection unit 130 may determine that roaming has occurred.

Referring to FIG. 2 again, based on it being determined in step S103 that the user may be located indoors, the roaming detection unit 130 may perform determining whether the location of the user may be in a building for predetermined use (S104).

Here, the building for the predetermined use means a building for use that may perform actions such as hovering around, rapidly changing the walking speed, and moving the same road even though the user may not be in the roaming state. For example, the building for the predetermined use may include one or more of the user's home, religious facilities, sales facilities, medical facilities, exercise facilities, recreational facilities, tourism and resting facilities, public institutions, and buildings with experience of visiting. However, the present disclosure is not limited thereto.

Based on it being determined that the user may be located indoors through step S103, and based on the location of the user being determined to be a shopping mall (sale facility) through step S104, the roaming detection unit 130 may determine a current state of the user as a normal state even though the user may be determined to be in the roaming state through the convex shell algorithm (S105).

Based on it being determined in step S104 that the location of the user may not be the building for the predetermined use, the roaming detection unit 130 may determine whether the building where the user may be located may be a building where the user has previously visited in consideration of the location data of the user (S106). Here, based on the user being located in a building that has been visited even though it may not be the building for the predetermined use, the current state may be determined as the normal state.

Here, information on the building that has been visited may be pre-stored by an administrator who monitors whether roaming has occurred by receiving whether the roaming has been detected from the roaming detection server 100, and a guardian who protects and manages the user. The information on the building that has been visited may be updated through step S110, which will be described later.

In addition, through step S106, based on the current location of the user being a building for no visit experience, the roaming detection unit 130 may determine whether he/she stays for a predetermined time or more in that building, and determine that roaming has occurred based on he/she staying longer than the predetermined time. Here, based on it being within the predetermined time, the roaming detection unit 130 may register the current location of the user as a new place and designate a building that have been visited (S110). By doing so, it may be determined that the user may be in the normal state based on the user visiting the place again.

Based on, in step S103, it being determined that the location of the user may be outdoor, the roaming detection unit 130 may detect whether the user may be roaming by checking whether the user satisfies the predetermined condition using the convex hull algorithm (S111).

In other words, in the case of the conventional method for detecting roaming, based on one being located indoors where it may be difficult to accurately obtain location data from the user, in some embodiments, based on one being located inside a building where the indoor positioning system may not be built, it may be determined that the location of the user does not change, so that the user may be staying in a certain area. Based on a predetermined time exceeded in this state, regardless of whether actual roaming has occurred, it may be inevitable to detect that the roaming has occurred. However, in the roaming detection server 100 according to the embodiment of the present disclosure, based on one being located indoors where it may be difficult to accurately obtain the location data from the user, the roaming detection unit 130 determines whether it may be safe to stay for a long time depending on the use or purpose of the building in which one may be located, and detects whether the roaming has occurred. Even in a building without the indoor positioning system, it may be possible to prevent the user from inadvertently detecting that the roaming has occurred due to the user staying in a certain area for a predetermined period of time.

In an embodiment, the roaming detection unit 130 may calculate an average walking speed of the user using walking speed data of the user, and detect whether the user's roaming occurs by comparing the calculated average walking speed with the walking speed data of the user measured in real-time. Hereinafter, with reference to FIG. 4, a configuration in which the roaming detection server 100 according to the embodiment of the present disclosure detects roaming using the walking speed of the user will be described.

Figure 4:
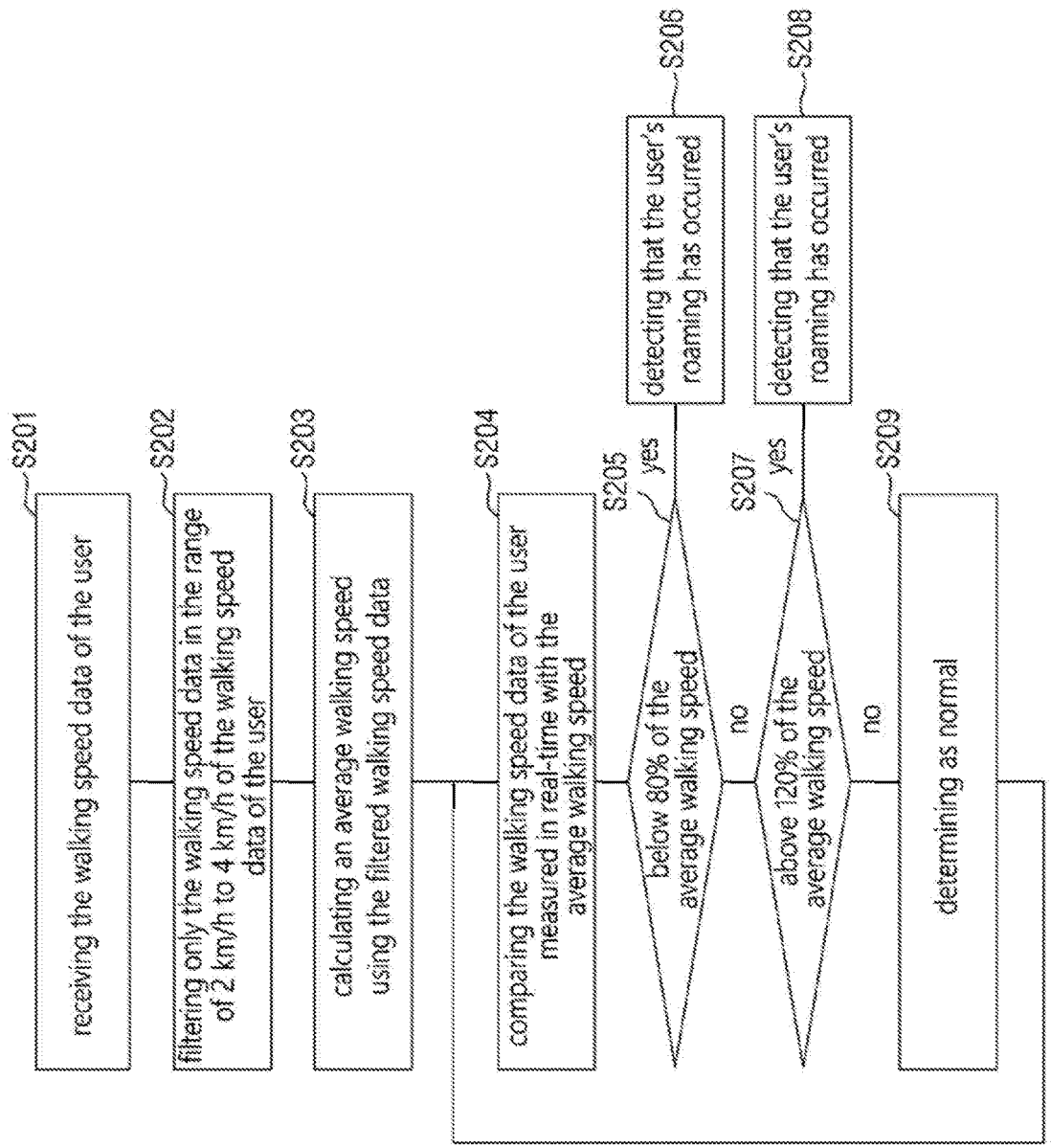
FIG. 4 is a flowchart for explaining a configuration in which the roaming detection server 100 according to the embodiment of the present disclosure detects roaming using a walking speed of a user.

FIG. 4 is a flowchart for explaining a configuration in which the roaming detection server 100 according to the embodiment of the present disclosure detects roaming using a walking speed of a user.

Referring to FIG. 4, first, the interface 110 may perform receiving the walking speed data of the user from the user terminal 10 (S201). For example, the user terminal 10 may calculate the amount of location change per hour of the user using location data measured through the GPS sensor and location data measured from the indoor positioning system provided in a building, and the interface 110 may receive the calculated location change per hour, that is, the walking speed data. However, it is not limited thereto, and the roaming detection unit 130 may calculate the walking speed of the user by using the location data of the user received through the interface 110.

In another embodiment, the interface 110 may receive the number of steps data of the user from the user terminal 10, and the roaming detection unit 130 may calculate the walking speed data using the number of steps, a stride length of the user, and time information.

Next, the roaming detection unit 130 may perform filtering the walking speed data in the range of 2 km/h to 4 km/h of the walking speed data of the user received in step S202. Here, the roaming detection unit 130 may calculate the average walking speed of the user by using the filtered walking speed data ranging from 2 km/h to 4 km/h.

In a study conducted in the United States in 2011 (Studenski, S., Perera, S., Patel, K., Rosano, C., Faulkner, K., Inzitari, M., . . . Guralnik, J. (2011). Gait speed and survival in older adults. JAMA, 305(1), 50-58.), walking speeds of 34,486 people were analyzed from 1986 to 2000, and the average walking speed of people was 0.9 m/s or 3.24 km/h. In addition, the results of a study of 2222 people at Ansan Hospital of Korea University (Lee, S., & Shin, C. (2017). Interaction of obstructive sleep apnea and cognitive impairment with slow gait speed in middle-aged and older adults. Age and Ageing, 46(4), 653-659.) also showed that the average of people was 1.0 m/s, that is, 3.6 km/h (however, the study conducted at Ansan Hospital of Korea University considers that an average age may be about 10 years lower than in the US study).

Considering this, a speed of 3 km/h to 4 km/h may be regarded as a state in which the user has not exercised, and based on a speed being higher than the one calculated, it may be recognized as an exercise state. Also, a completely inactive state may be less than 1 km/h, which may be half a speed of a non-exercise state. A value in the range of 2 km/h to 4 km/h, which may be a value between the exercise state and the complete inactive state, may be recognized as a state in which the user performs general activities.

In other words, the roaming detection server 100 according to the embodiment of the present disclosure may filter and use the walking speed data in the range of 2 km/h to 4 km/h in which the user performs the general activities, thereby detecting roaming more accurately based on the walking speed.

Thereafter, it may receive the walking speed data of the user in real-time through the interface 110, and the roaming detection unit 130 may perform comparing the walking speed of the user measured in real-time with the average walking speed calculated in step S203 (S204). Here, the roaming detection unit 130 may determine whether the walking speed data of the user measured in real-time falls below 80% of the calculated average walking speed (S205), and based on it falling below 80% compared to the calculated average walking speed, it may detect that roaming has occurred (S206). Based on the walking speed data of the user being more than 80% of the calculated average walking speed, the roaming detection unit 130 determines whether the walking speed data of the user rises by 120% or more compared to the calculated average walking speed (S207), and based on it rising to 120% or more compared to the calculated average walking speed, it may detect that roaming has occurred (S208). Based on, in step S207, the walking speed data of the user being less than 120% of the calculated average walking speed, the roaming detection unit 130 may determine that it may be the normal state (S209), that is, no roaming has occurred. In other words, based on the walking speed of the user falling within the range of 80% to 120% of the average walking speed, the roaming detection unit 130 may determine the user as normal, and based on it falling within a range other than that, it may make a roaming decision.

In an embodiment, the roaming detection unit 130 may calculate an average heart rate of the user using the heart rate data, and compare the calculated average heart rate with the heart rate data of the user measured in real-time to detect whether the user's roaming has occurred. Hereinafter, with reference to FIG. 5, a configuration in which the roaming detection server 100 according to the embodiment of the present disclosure detects roaming using the heart rate data of the user will be described.

Figure 5:
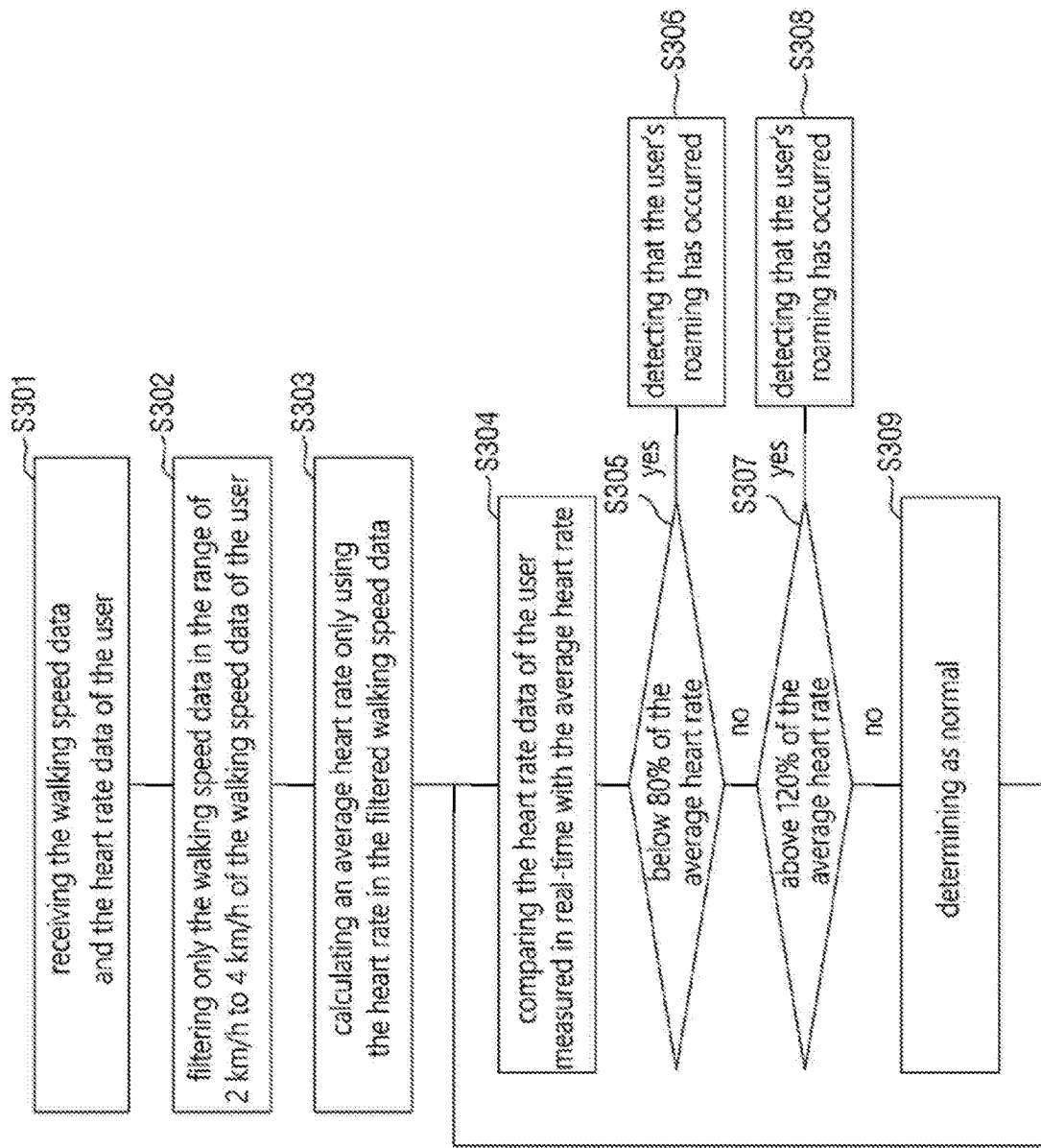
FIG. 5 is a flowchart for explaining a configuration in which the roaming detection server 100 according to the embodiment of the present disclosure detects roaming using a heart rate of the user.

FIG. 5 is a flowchart for explaining a configuration in which the roaming detection server 100 according to the embodiment of the present disclosure detects roaming using a heart rate of the user.

Referring to FIG. 5, first, receiving the walking speed data and the heart rate data of the user through the interface 110 may be performed (S301). For example, the user terminal 10 may be a wearable device worn on a body such as the user's wrist, and may receive the heart rate data measured via the wearable device. However, it is not limited thereto, and any method for receiving the heart rate data of the user may be applied. Here, the configuration of receiving the walking speed data may be the same as the configuration performed in step S201 of FIG. 4.

Thereafter, the roaming detection unit 130 may perform filtering the walking speed data in the range of 2 km/h to 4 km/h among the walking speed data of the user (S302), and perform calculating the average heart rate using the heart rate data in the filtered walking speed data (S303).

Here, in order to calculate the average heart rate of the user in the general activity state, not the exercise state and the complete inactivity state, the heart rate data in the walking speed data in the range of 2 km/h to 4 km/h of the user may be used.

Next, the interface 110 may receive the heart rate data of the user measured in real-time from the user terminal 10, and the roaming detection unit 130 may perform comparing the heart rate data of the user measured in real-time with the average heart rate (S304). Here, the roaming detection unit 130 may determine whether the heart rate data of the user measured in real-time falls below 80% of the calculated average heart rate (S305), and based on it falling below 80% of the calculated average heart rate, it may detect that roaming has occurred (S306). Based on the heart rate data of the user measured in real-time being 80% or more of the calculated average heart rate, the roaming detection unit 130 may determine whether the heart rate data of the user rises above 120% compared to the calculated average heart rate (S307), and based on it rising above 120% compared to the calculated average heart rate, it may detect that roaming has occurred (S308). Based on, in step S307, the heart rate data of the user being less than 120% of the calculated average heart rate, the roaming detection unit 130 may determine that the user's state may be normal, that is, no roaming has occurred. In other words, based on the user's heart rate falling within the range of 80% to 120% of the average heart rate, the roaming detection unit 130 may determine the user as normal, and based on it falling within a range other than that, it may make a roaming decision.

In other words, the roaming detection unit 130 may detect whether the user's roaming has occurred by using at least one of the walking speed of the user and the user's heart rate as well as the use or purpose of the building where the user may be located. Here, the roaming detection unit 130 may use all of the use or purpose of the building where the user may be located, the walking speed of the user, and the user's heart rate. For example, based on the user being located indoors, it may be primarily determined whether the roaming has occurred using the use or purpose of the building where the user may be located, and verify whether the roaming has occurred primarily determined using the walking speed and the heart rate of the user, thereby calculating a more accurate and reliable result value.

In an embodiment, the interface 110 may receive the gait data including the walking speed data and walking direction data from the user terminal 10. The roaming detection unit 130 may calculate the walking index using the gait data, generate the gait model that learns the calculated walking index using deep Learning, and detect whether the user's roaming has occurred using the generated gait model. Hereinafter, with reference to FIGS. 6 to 12, a configuration in which the roaming detection server 100 according to the embodiment of the present disclosure uses the gait model to detect whether the user's roaming has occurred will be described.

Figure 6:
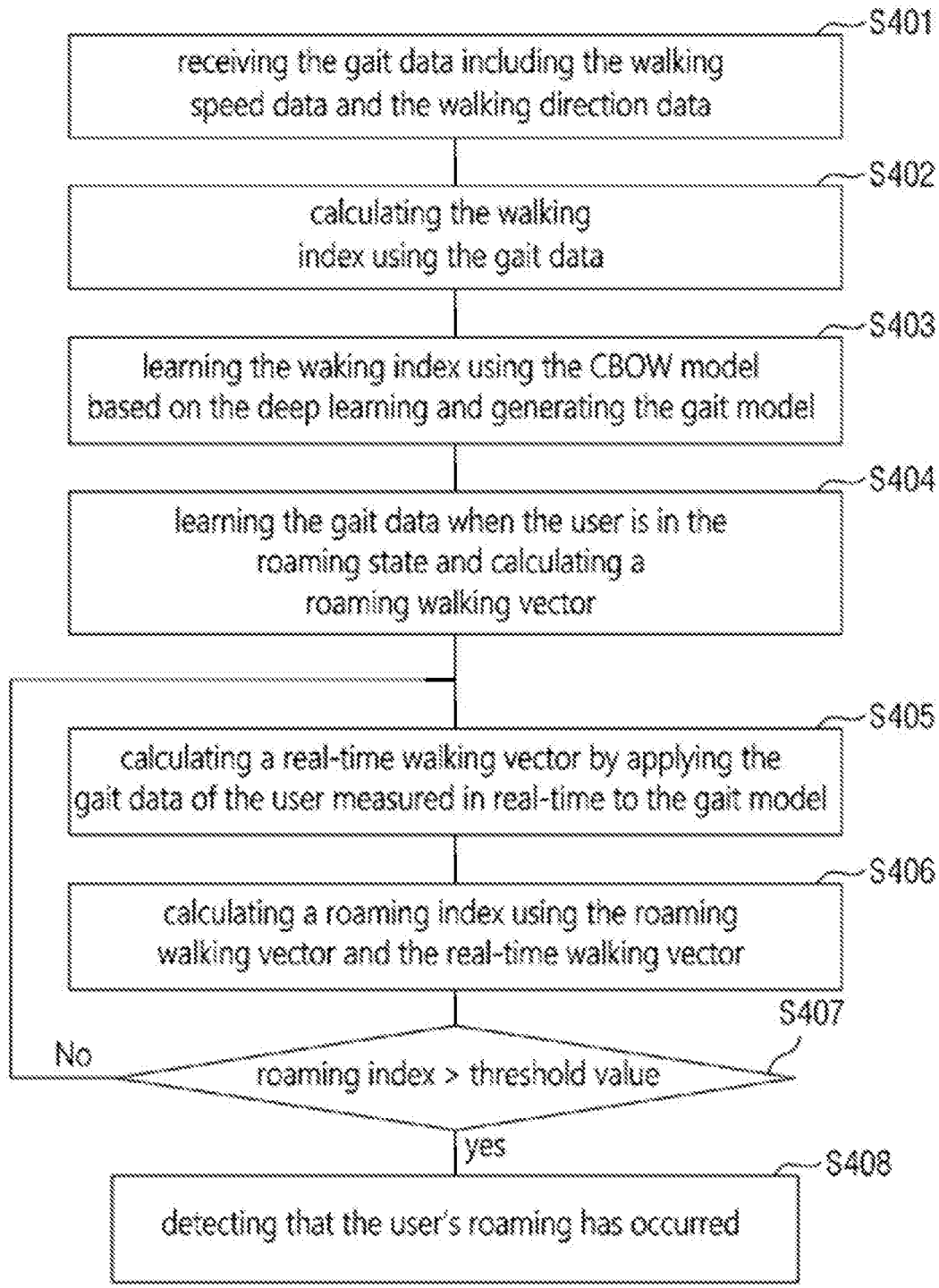
FIG. 6 is a flowchart for explaining a configuration in which the roaming detection server 100 according to the embodiment of the present disclosure detects roaming using a gait model generated from gait data of the user.

FIG. 6 is a flowchart for explaining a configuration in which the roaming detection server 100 according to the embodiment of the present disclosure detects roaming using a gait model generated from gait data of the user.

Referring to FIG. 6, first, receiving the gait data including the walking speed data and the walking direction data from the user terminal 10 through the interface 110 may be performed (S401).

Thereafter, the roaming detection unit 130 may perform calculating the walking index using the gait data received in step S401 (S402). Hereinafter, it will be described with reference to FIGS. 7 to 10.

Figure 7:
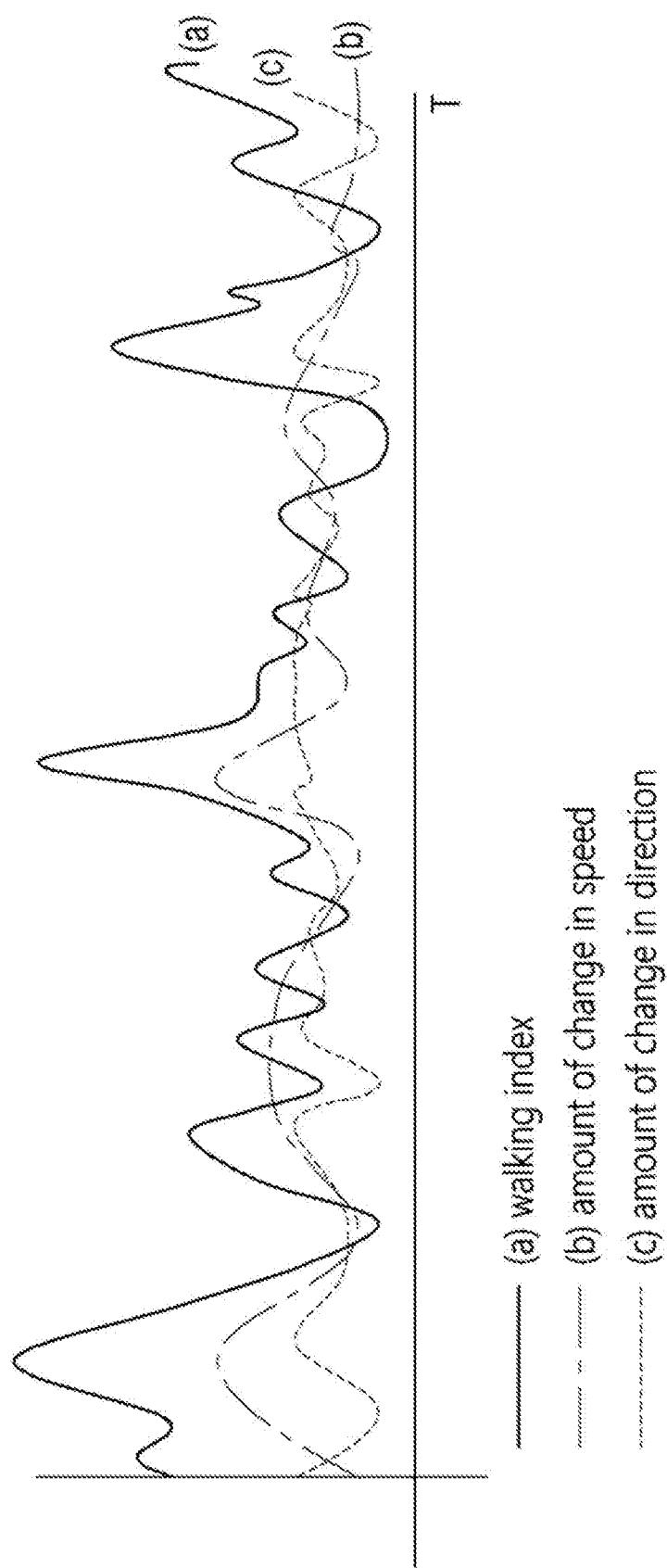
FIG. 7 is a graph for explaining a relationship between a speed change amount and a direction change amount and a walking index in the roaming detection server 100 according to the embodiment of the present disclosure.

FIG. 7 is a graph for explaining a relationship between a speed change amount and a direction change amount and a walking index in the roaming detection server 100 according to the embodiment of the present disclosure.

Referring to FIG. 7, calculating the walking index, the roaming detection unit 130 may calculate the walking index using Equation 1 below:

$$\text{walking index} = (\text{amount of change in direction} + \alpha) \times (\text{amount of change in speed} + \beta)$$

where $\alpha$ and $\beta$ are arbitrary constant values exceeding 1. $\alpha$ and $\beta$ may be arbitrarily set to exceed 1, and the amount of change in direction and the amount of change in speed may not be 0. For example, based on the user not changing the direction, the amount of change in direction may be zero.

The walking index may be calculated as 0. The roaming detection unit 130 may prevent the walking index from being calculated as 0 based on the amount of change being 0 by adding α and β to the amount of change in direction and the amount of change in speed based on calculating the walking index.

The roaming detecting unit 130 may calculate the walking index per unit time using the gait data and Equation 1 above. Here, the walking index may be a product of the amount of change in direction and the amount of change in speed as shown in the graph of FIG. 7, and may be time series data that changes over time.

Hereinafter, with reference to FIGS. 8 and 9, a configuration for calculating the amount of change in direction and the amount of change in speed for calculating the walking index will be described.

Figure 8:
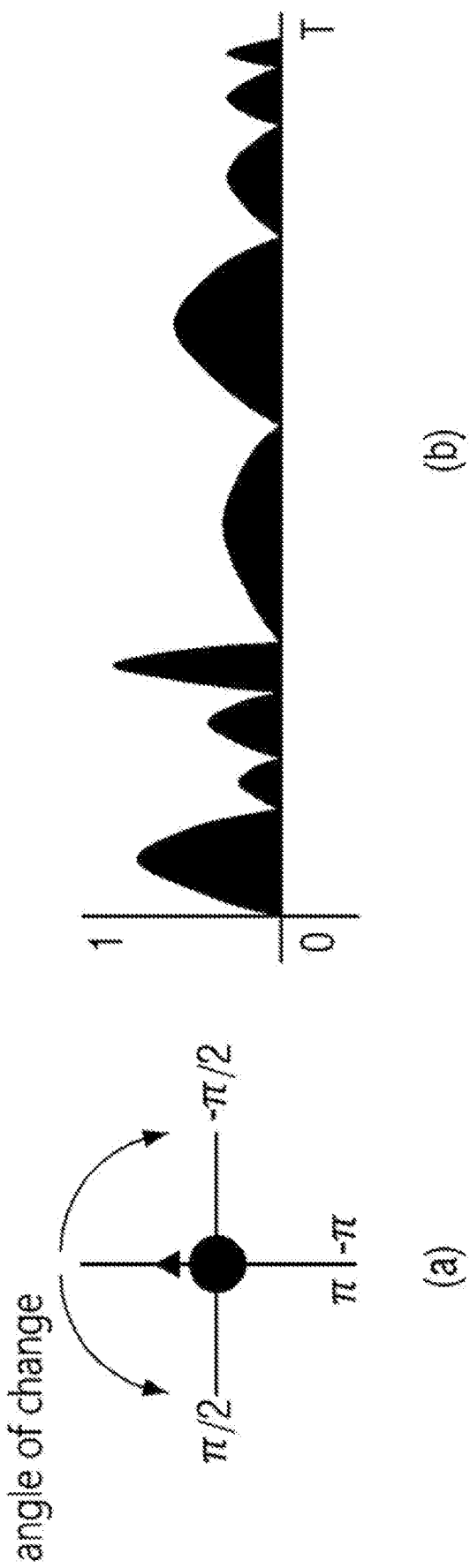
FIG. 8 is a graph for explaining a configuration in which the roaming detection server 100 according to the embodiment of the present disclosure calculates the direction change amount.

FIG. 8 is a graph for explaining a configuration in which the roaming detection server 100 according to the embodiment of the present disclosure calculates the direction change amount.

Referring to FIG. 8, the roaming detection unit 130 may calculate the amount of change in direction for calculating the walking index using Equation 2 below:

$$\text{amount of change in direction} = \int_{t-1}^{t} |\text{angle of change (rad)}/\pi|$$

where t may be a current measurement time point, and t−1 may be a previous measurement time point.

The amount of change in direction may be a cumulative value of change in direction between a time point to be measured (current measurement time point, t) and the previous measurement time point t−1, and may be calculated as an integral value of an angle of change of a direction with respect to time change.

Figure 9:
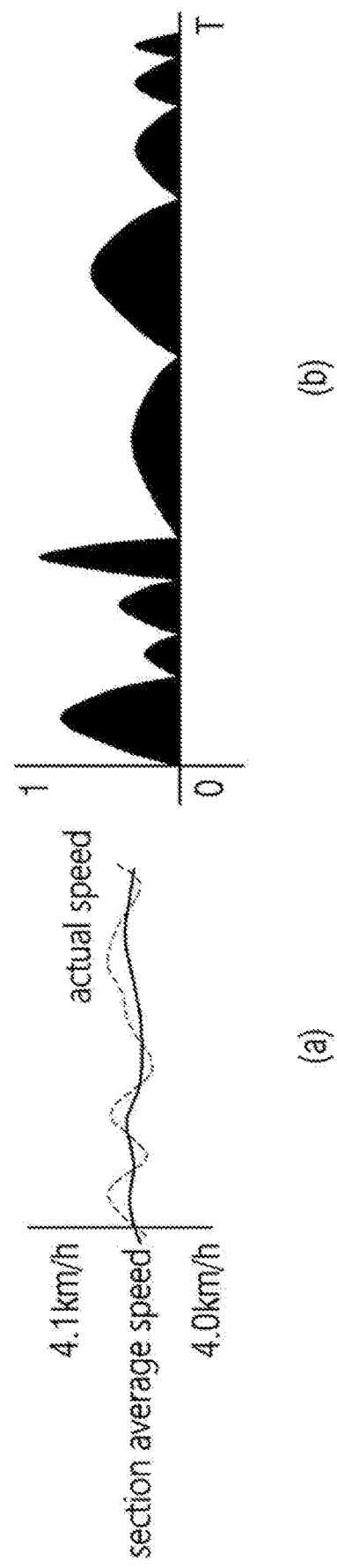
FIG. 9 is a graph for explaining a configuration in which the roaming detection server 100 according to the embodiment of the present disclosure calculates the speed change amount.

FIG. 9 is a graph for explaining a configuration in which the roaming detection server 100 according to the embodiment of the present disclosure calculates the speed change amount.

Referring to FIG. 9, the roaming detection unit 130 may calculate the amount of change in speed for calculating the walking index using Equation 3 below:

$$\text{amount of change in speed} = \int_{t-1}^{t} |\text{average walking speed} - \text{real-time walking speed}(t)|$$

where t may be a current measurement time point, and t−1 may be a previous measurement time point.

The amount of change in speed may be a cumulative value of the difference between the average walking speed between the current measurement time point t and the previous measurement time point t−1 and the walking speed at the current measurement time point t (real-time walking speed). It may be calculated as an integral value of the speed change over time.

Here, the average walking speed may calculate the average walking speed using the gait data including the walking speed data having a walking speed of 2 km/h to 4 km/h among the gait data of the user.

Referring back to FIG. 6, the roaming detection unit 130 may perform generating the gait model represented by an N-dimensional vector by learning a quantized walking index using a CBOW (Continuous Bag-of-Word) model based on the deep learning (S403). Hereinafter, it will be described with reference to FIGS. 10 to 11.

Figure 10:
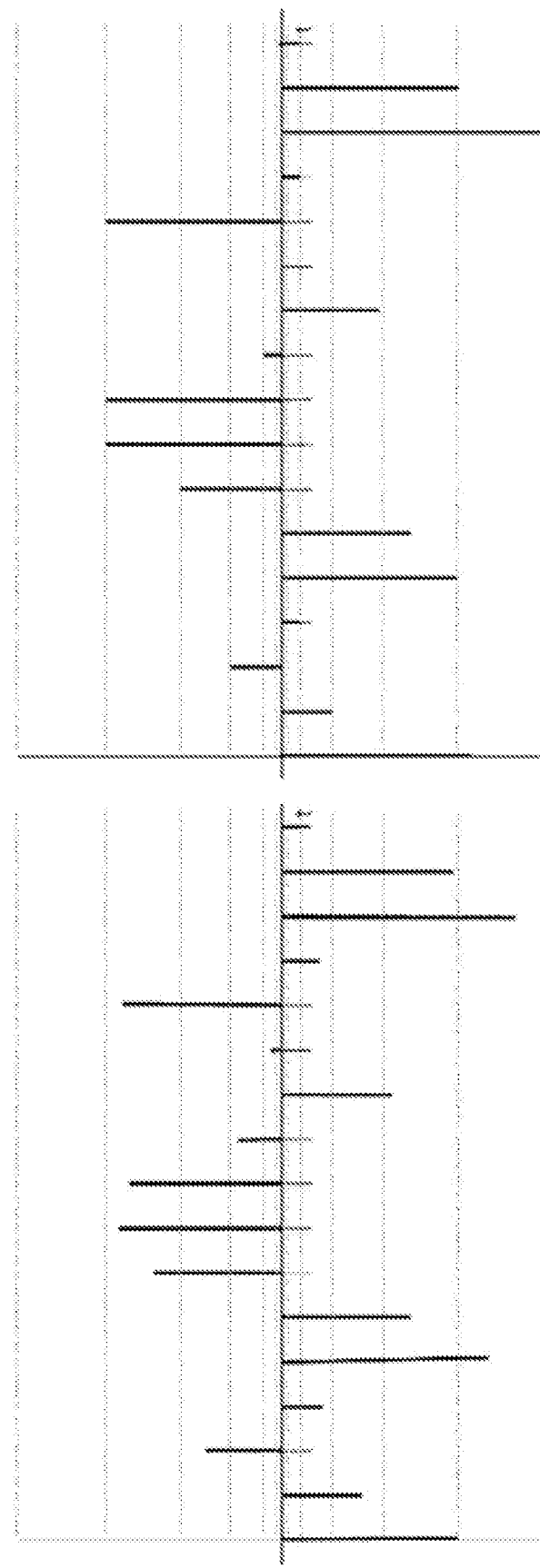
FIG. 10 is a graph for showing the walking index quantized by the roaming detection server 100 according to the embodiment of the present disclosure.

FIG. 10 is a graph showing the walking index quantized by the roaming detection server 100 according to the embodiment of the present disclosure.

Referring to FIG. 10, first, the roaming detection unit 130 of the roaming detection server 100 may quantize the walking index calculated through Equations 1 to 3 above, thereby stringing the walking index of a time series. Here, the walking index may be symbolized using a Gaussian distribution. For example, the roaming detection unit 130 may obtain the gait data in the form of "1 2 4 A E C 9 B 1 2 5 . . . " by quantizing the walking index.

Figure 11:
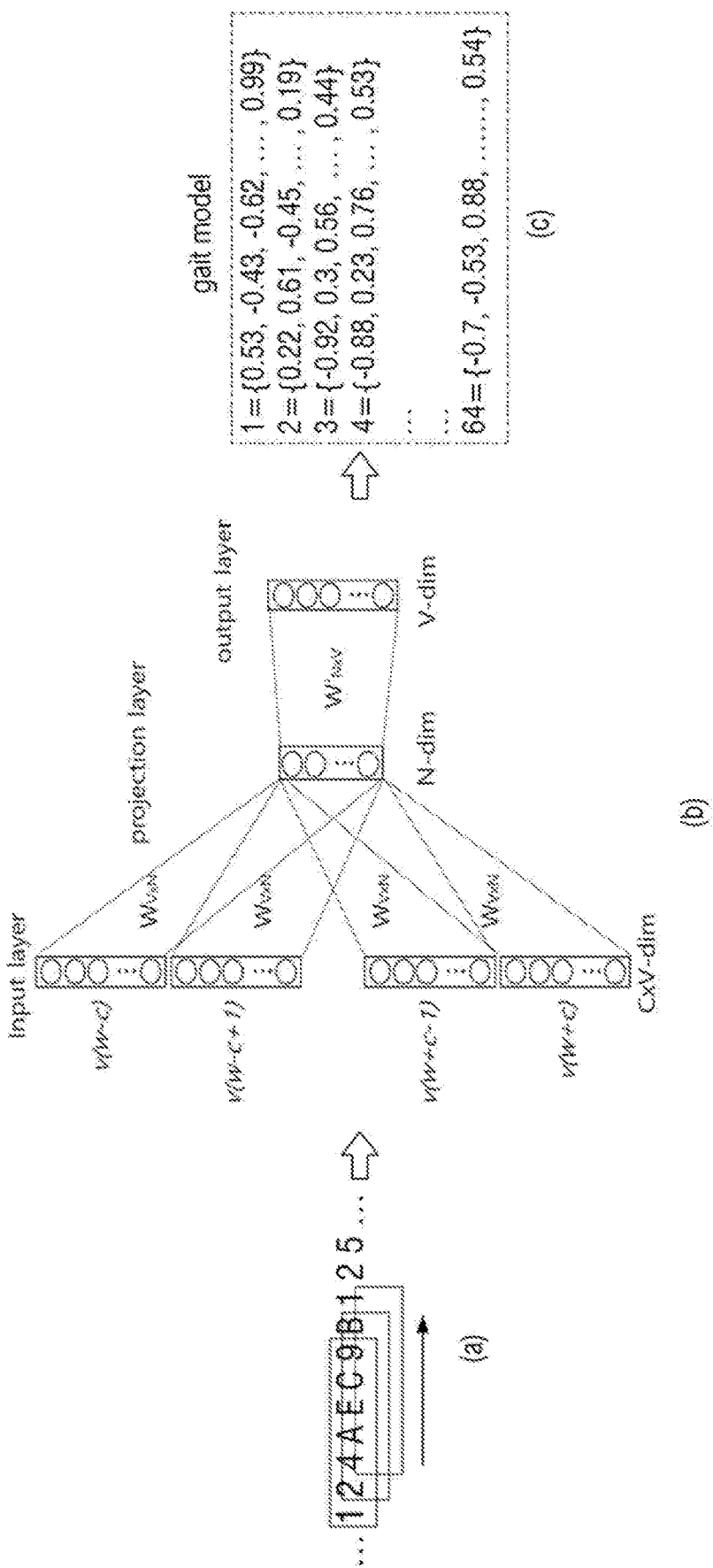
FIG. 11 is a view for explaining the gait model generated in the roaming detection server 100 according to the embodiment of the present disclosure.

FIG. 11 is a view for explaining the gait model generated in the roaming detection server 100 according to the embodiment of the present disclosure.

Referring to FIG. 11, the roaming detection unit 130 may train the gait data obtained in the above manner by using the CBOW (Continuous Bag-of-Word) model based on the deep learning. Here, the CBOW model means a deep learning model that learns the context of data and vectorizes each pattern in the data to generate a vector table for the entire pattern.

Here, the roaming detection unit 130 may move each unit data included in the data of the form "1 2 4 A E C 9 B 1 2 5 . . . " by a window (FIG. 11A) and input data to a neural network structure of the CBOW (FIG. 11B), thereby generating the gait model represented by the N-dimensional vector (FIG. 11C).

Referring back to FIG. 6, the roaming detecting unit 130 may perform learning the gait data based on the user being in the roaming state and calculating a roaming walking vector using the gait model (S404), and perform calculating a real-time walking vector by applying the gait data of the user measured in real-time to the gait model (S405). Hereinafter, it will be described with reference to FIG. 12.

Figure 12:
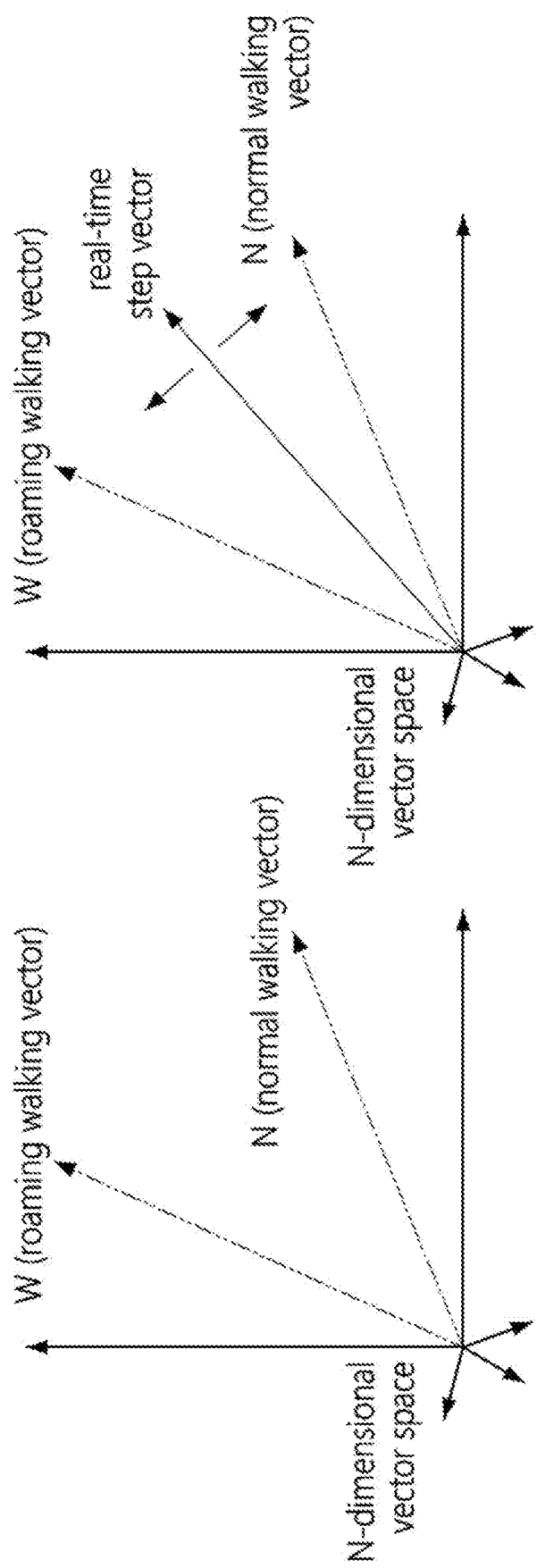
FIG. 12 is a graph showing a form in which real-time gait data of the user is applied to the gait model and vectorized, and the vectorized real-time gait data is displayed in a vector space in the roaming detection server 100 according to the embodiment of the present disclosure.

FIG. 12 is a graph showing a form in which real-time gait data of the user may be applied to the gait model and vectorized, and the vectorized real-time gait data may be displayed in a vector space in the roaming detection server 100 according to the embodiment of the present disclosure.

Referring to FIG. 12, the roaming detecting unit 130 may use the gait model to learn the gait data based on the user being in the roaming state, and calculate the roaming walking vector as a result value of learning. In addition, the roaming detecting unit 130 may use the gait model to learn the gait data based on the user being in the normal state, and calculate the roaming walking vector as a result value of learning. For example, the roaming detection unit 130 may receive the gait data of the user at a time based on the roaming being detected, and apply the received gait data to the gait model, thereby generating normal gait learning data in the form of "1 3 3 A B C 9 B 1 2 2 . . . " for gait based on being in the normal state. In addition, the roaming detection unit 130 may receive the gait data of the user at a time based on the roaming not being detected, and apply the received gait data to the gait model, thereby generate roaming gait learning data in the form of "1 2 4 A E C 9 B 1 2 5 . . . " for gait based on being in the roaming state. The roaming sensing unit 130 may calculate the N-dimensional vector by applying the normal gait learning data and the roaming gait learning data generated as described above to the gait model as illustrated in FIG. 12A.

Thereafter, the interface 110 may receive the gait data of the user measured in real-time, and the roaming detection unit 130 may apply the gait data of the user measured in real-time to the gait model, thereby calculating the real-time walking vector as shown in FIG. 12B.

Next, referring back to FIG. 6, the roaming detection unit 130 may perform calculating a roaming index using the roaming walking vector and the real-time walking vector (S406).

In an embodiment, the roaming detection unit 130 may calculate the roaming index using Equation 4 below in t calculating the roaming index:

roaming index=1/|real-time walking vector−roaming walking vector| where the roaming index may be a value inversely proportional to a vector distance between the real-time walking vector and the roaming vector, and may be a value inversely proportional to an angular distance between the real-time walking vector and the roaming walking vector.

The roaming detection unit 130 may calculate a distance between the real-time walking vector and the roaming walking vector using cosine similarity, and calculate the roaming index using the calculated distance between the real-time walking vector and the roaming walking vector.

Thereafter, the roaming detection unit 130 may perform comparing the calculated roaming index with a threshold value (S407).

The real-time walking vector oscillates between the roaming walking vector W and the normal walking vector N, as shown in FIG. 12B. The distance between the real-time walking vector and the roaring walking vector varies, and the roaming index fluctuates inversely. The roaming detection unit 130 may continuously monitor the roaming index that fluctuates, and based on the roaming index exceeding a predetermined threshold value, that is, based on it falling below an angular distance roaming threshold between the real-time walking vector and the roaming walking vector, it may determine that the roaming has occurred (S408).

In other words, the roaming sensor 130 generates a personalized gait model using the gait data including the walking speed and the gait direction data of the user, and continuously monitors the user's condition and detects the roaming using it. A more accurate result value may be output in that it may be possible to diagnose the roaming using the personalized gait model without determining the roaming on a uniform basis for a plurality of users.

The methods according to the embodiments of the present disclosure described so far may be performed by execution of a computer program implemented in computer readable code. The computer program may be transmitted to and installed on the second computing device from the first computing device via a network such as the Internet, and may be used in the second computing device. The first computing device and the second computing device include all of a server device, a physical server belonging to a server pool for cloud services, and a stationary computing device such as a desktop PC.

The computer program may be stored in a recording medium such as a DVD-ROM or a flash memory device.

In the above description, it is described that all the components constituting the embodiments of the present disclosure are combined or operated as one, but the technical features of the present disclosure are not limited to these embodiments. That is, within the scope of the present disclosure, all of the components may be selectively combined and operated in one or more combinations.

Although the operations are shown in an order in the drawings, those skilled in the art will appreciate that many variations and modifications can be made to the embodiments without substantially departing from the principles of the presently disclosed technology. The disclosed embodiments of the presently disclosed technology are used in a generic and descriptive sense and not for purposes of limitation. The scope of protection of the present presently disclosed technology should be interpreted by the following claims, and all technical ideas within the scope equivalent thereto should be construed as being included in the scope of the technical idea defined by the present disclosure.

What is claimed is:

1. A method for detecting whether a user's roaming has occurred, the method being performed by a roaming detection server, and comprising:

receiving location data of the user from a terminal of the user;

determining whether the user is located indoors by using the location data of the user, and determining a use of a building in which the user is located using use information of the building based on the user being located indoors; and detecting whether the user's roaming has occurred based on a predetermined condition, wherein it is detected that the roaming has occurred based on the building in which the user is located not being a building of a predetermined use, wherein the detecting further comprises:

calculating a walking index using the user's gait data, generating a gait model for learning the calculated walking index using machine learning, and detecting whether the user's roaming has occurred using the generated gait model; and calculating the walking index using Equation 1 below:

walking index=(amount of change in direction+α)× (amount of change in speed+β)

where, the α and β are arbitrary constant values exceeding 1.

2. The method of claim 1, wherein the determining comprises determining the use of the building in which the user is located using a geographic information system (GIS) included in the use information of the building.

3. The method of claim 1, wherein the detecting comprises detecting whether the user's roaming has occurred using a convex hull algorithm.

4. The method of claim 1, wherein the building of the predetermined use comprises at least one of the user's home, religious facilities, sales facilities, medical facilities, exercise facilities, recreational facilities, tourism and resting facilities, public institutions, and buildings with experience of visiting.

5. The method of claim 1, wherein the receiving comprises receiving walking speed data of the user from the terminal of the user, and wherein the detecting comprises calculating an average walking speed of the user using the walking speed data, and detecting whether the user's roaming has occurred by comparing the calculated average walking speed with the walking speed data of the user measured in real-time.

6. The method of claim 5, wherein detecting whether the user's roaming has occurred by comparing the calculated average walking speed with the walking speed data of the user measured in real-time comprises:

filtering the walking speed data in the range of 2 km/h to 4 km/h of the received walking speed data of the user, and calculating the average walking speed using the filtered walking speed data; and determining that the roaming has occurred based on the walking speed data of the user measured in real-time falling below 80% or rises above 120% compared to the calculated average walking speed.

7. The method of claim 5, wherein the receiving further comprises receiving heart rate data of the user from the terminal of the user, and
wherein the detecting further comprises calculating an average heart rate of the user using the heart rate data, and comparing the calculated average heart rate and the heart rate data of the user measured in real-time to detect whether the user's roaming has occurred.

8. The method of claim 7, wherein comparing the calculated average heart rate and the heart rate data of the user measured in real-time to detect whether the user's roaming has occurred comprises:
calculating the average heart rate using the heart rate data of the user in the calculated average walking speed; and
determining that the user's roaming has occurred based on the heart rate data of the user measured in real-time falling below 80% or rises above 120% compared to the calculated average heart rate.

9. The method of claim 1, wherein the receiving further comprises receiving gait data including walking speed data and walking direction data of the user from the terminal of the user.

10. The method of claim 1, wherein the detecting further comprises calculating the amount of change in direction using Equation 2 below:

$$\text{amount of change in direction} = \int_{t-1}^{t} |\text{angle of change (rad)}/\pi|$$

where, the t is a current measurement time point, and the t−1 is a previous measurement time point.

11. The method of claim 1, wherein the detecting further comprises calculating the amount of change in speed using Equation 3 below:

$$\text{amount of change in speed} = \int_{t-1}^{t} |\text{average walking speed} - \text{real-time walking speed(t)}|$$

where, the t is a current measurement time point, and the t−1 is a previous measurement time point.
wherein calculating the amount of change in speed comprises calculating an average walking speed using 2 km/h to 4 km/h or less of the walking speed data.

12. The method of claim 9, wherein the detecting further comprises:
quantizing the calculated walking index; and
generating the gait model represented by an N-dimensional vector by learning the quantized walking index using a CBOW (Continuous Bag-of-Word) model based on deep learning.

13. The method of claim 12, wherein the detecting further comprises:
using the gait model to learn gait data based on the user being in a roaming state, and calculating a roaming walking vector as a result value of learning;
calculating a real-time walking vector using the gait data of the user measured in real-time as an input value of the gait model;
calculating a roaming index using the roaming walking vector and the real-time walking vector; and
determining that the roaming has occurred based on the roaming index exceeding a predetermined threshold value.

14. The method of claim 13, wherein calculating the roaming index using the roaming walking vector and the real-time walking vector comprises calculating the roaming index using Equation 4 below:

roaming index=1/|real-time walking vector−roaming walking vector|

15. A roaming detection server, comprising:
an interface for receiving location data of a user from a terminal of the user;
a location determination unit for determining whether the user is located indoors by using the location data of the user, and determining a use of a building in which the user is located using use information of the building based on the user being located indoors; and
a roaming detection unit for detecting whether the user's roaming has occurred based on a predetermined condition, wherein it is detected that the roaming has occurred based on the building in which the user is located not being a building of a predetermined use,
wherein the roaming detection unit calculates a walking index using the user's gait data, generates a gait model for learning the calculated walking index using machine learning, detects whether the user's roaming has occurred using the generated gait model, and calculates the walking index using Equation 1 below:

walking index=(amount of change in direction+α)× (amount of change in speed+β)

where, the α and β are arbitrary constant values exceeding 1.

16. The system of claim 15, wherein the determining comprises determining the use of the building in which the user is located using a geographic information system (GIS) included in the use information of the building.

17. The system of claim 15, wherein the detecting comprises detecting whether the user's roaming has occurred using a convex hull algorithm.

18. The system of claim 15, wherein the building of the predetermined use comprises at least one of the user's home, religious facilities, sales facilities, medical facilities, exercise facilities, recreational facilities, tourism and resting facilities, public institutions, and buildings with experience of visiting.

19. The system of claim 15, wherein the receiving comprises receiving walking speed data of the user from the terminal of the user, and
wherein the detecting comprises calculating an average walking speed of the user using the walking speed data, and detecting whether the user's roaming has occurred by comparing the calculated average walking speed with the walking speed data of the user measured in real-time.

20. The system of claim 15, wherein the receiving further comprises receiving gait data including walking speed data and walking direction data of the user from the terminal of the user.

* * * * *